US00PP25652P3

(12) United States Plant Patent
Clark et al.

(10) Patent No.: US PP25,652 P3
(45) Date of Patent: Jun. 23, 2015

(54) COLEUS PLANT NAMED 'UF12-6-2'

(50) Latin Name: *Plectranthus scutellarioides*
Varietal Denomination: UF12-6-2

(71) Applicant: Florida Foundation Seed Producers, Inc., Marianna, FL (US)

(72) Inventors: David G. Clark, Gainesville, FL (US); Grayson M. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 160 days.

(21) Appl. No.: 13/986,165

(22) Filed: Apr. 5, 2013

(65) Prior Publication Data

US 2014/0304874 P1 Oct. 9, 2014

(51) Int. Cl.
*A01H 5/12* (2006.01)
*A01H 5/02* (2006.01)

(52) U.S. Cl.
CPC ..... *A01H 5/02* (2013.01)
USPC ..... Plt./469; Plt./373

(58) Field of Classification Search
USPC ..... Plt./373, 469
See application file for complete search history.

(56) References Cited

PUBLICATIONS

U.S. Appl. No. 13/986,162, filed Apr. 5, 2013, Clark et al.
U.S. Appl. No. 13/986,166, filed Apr. 5, 2013, Clark et al.
U.S. Appl. No. 13/986,163, filed Apr. 5, 2013, Clark et al.
U.S. Appl. No. 13/986,161, filed Apr. 5, 2013, Clark et al.
U.S. Appl. No. 13/986,160, filed Apr. 5, 2013, Clark et al.
U.S. Appl. No. 13/986,164, filed Apr. 5, 2013, Clark at al.
Nguyen et al., "Genetics of growth habit and development of new coleus (*Solenosternon scutellarioides* (L.) Codd) varieties with trailing habit and bright color," *J. Heredity* 99:573-580, 2008.

*Primary Examiner* — Susan McCormick Ewoldt
(74) *Attorney, Agent, or Firm* — Dentons US LLP

(57) ABSTRACT

'UF12-6-2' is a new coleus plant distinguished by having coral pink-orange leaves trimmed in olive green, novel growth habit, and desirable late-flowering characteristics, as disclosed.

3 Drawing Sheets

Latin name of the genus and species of the plant claimed: *Plectranthus scutellarioides.*

Cultivar denomination: 'UF12-6-2'.

BACKGROUND OF THE INVENTION

The invention relates to a new and distinct cultivar of coleus plant named 'UF12-6-2'. 'UF12-6-2' originated from an open pollination conducted in May-November 2011 in Gainesville, Fla. between the female coleus plant 'UF10-40-14' (unpatented) and an unknown male coleus plant. A single seedling was chosen in May 2012 for further asexual propagation in Gainesville, Fla. (see FIG. 1 for pedigree).

'UF12-6-2' has been reproduced asexually for over one year through vegetative cuttings and has been found to retain its distinctive characteristics through successive asexual propagations.

UF12-6-2' has not been made publicly available more than one year prior to the filing date of this application.

When 'UF12-6-2' is compared to the female parent 'UF10-40-14' (unpatented), 'UF12-6-2' has foliage with coral pink-orange centers and olive green crenate leaf margins, while 'UF10-40-14' had leaves colored maroon with green serrated leaf margins. 'UF10-40-14" was eliminated from a breeding program in 2011 and is no longer in existence.

When 'UF12-6-2' is compared to the commercial cultivar 'Wizard Coral Sunrise', both plants have similar foliage color but 'Wizard Coral Sunrise' has a more upright growth habit (taller than wide), whereas 'UF12-6-2' is more compact with a more spreading growth habit (wider than tall). 'Wizard Coral Sunrise' also produces flowers much earlier than 'UF12-6-2', thus "UF12-6-2' retains more foliage over the course of a normal growing season in the garden.

SUMMARY OF THE INVENTION

The following are the most outstanding and distinguishing characteristics of 'UF12-6-2' when grown under normal horticultural practices in Gainesville, Fla. 'UF12-6-2' has a combination of novel growth habit, late season flowering, excellent heat tolerance, and consistent coral pink-orange edged in olive green foliage color that is significantly different than any other coleus plant in the trade. It has superior color stability in foliage in both sun and shade conditions, maintaining stable color in all conditions. It has a vigorous mounded spreading growth habit with excellent lateral branching when grown as a stock plant, thus providing ample vegetative propagules for producers. This plant has not been observed to set a significant number of flowers in any trial to date, thus it is desirable for long-season performance in the landscape, as coleus plants that set seed usually experience late season leaf drop.

BRIEF DESCRIPTION OF THE DRAWINGS

This new coleus plant is illustrated by the accompanying photographs, which show the plant's form and foliage. The colors shown are as true as can be reasonably obtained by conventional photographic procedures. The photographs were taken from 3-month-old plants grown from cuttings in 1-gallon pots during December 2012-March 2013 in greenhouses in Gainesville, Fla.

DETAILED BOTANICAL DESCRIPTION

Figure 1:
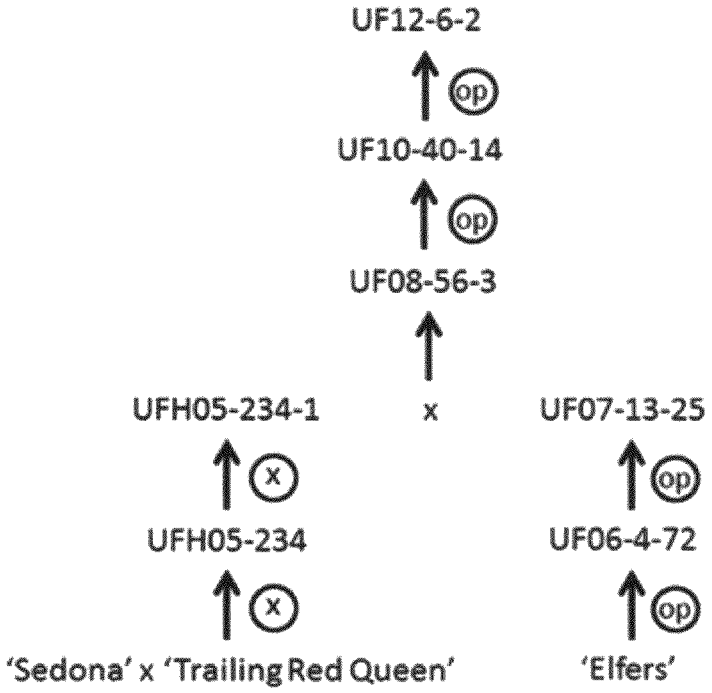
FIG. 1—shows the pedigree of the claimed plant.
Figure 2:
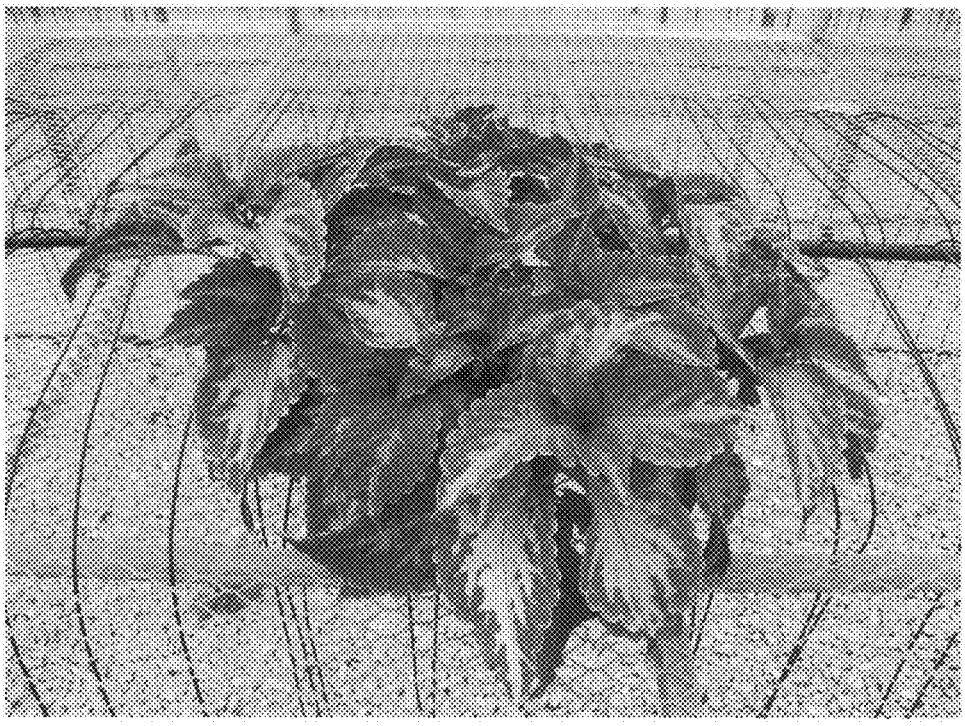
FIG. 2—shows the growth habit, form, and foliage of the claimed plant.
Figure 3:
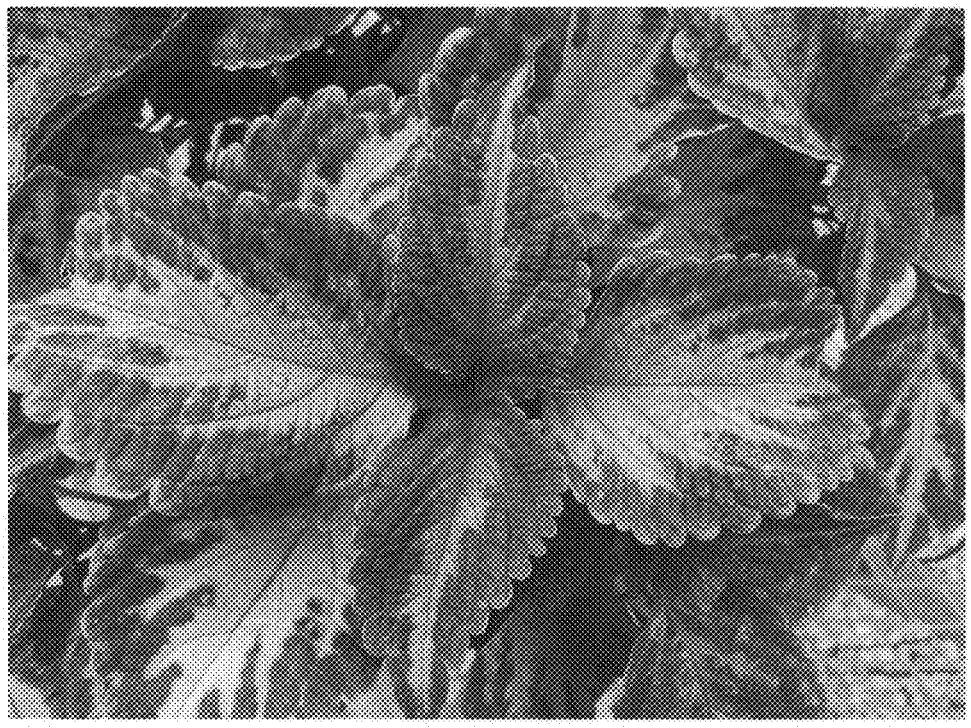
FIG. 3—shows a close-up of the foliage.

The following detailed description sets forth the distinctive characteristics of 'UF12-6-2'. The detailed description was taken on 3-month-old plants from cuttings growing in a glass greenhouse in Gainesville, Fla. in early spring 2013. The plants were pinched 2 weeks after cuttings were rooted, then grown in 1-gallon pots for approximately 10 weeks. Color references are to The R.H.S. Colour Chart of The Royal Horticultural Society of London (R.H.S.), 2007 5th Edition.

Classification:

*Family.*—Lamiaceae.

*Botanical.—Plectranthus scutellarioides.*

*Common name.*—Coleus.

*Cultivar name.*—'UF12-6-2'.

Plant description:

*Form.*—Spreading.

*Habit.*—Upright.

*Height* (*from top of soil*).—22 cm.

*Width* (*horizontal plant diameter*).—53 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant.*—6 main branches per plant with numerous side branches, pinched once.

*Branch color.*—RHS 144D.

*Texture*.—Smooth.

*Pubescence*.—Not present.

*Stem description.*—Square-shaped stem, 1.2 cm in diameter at the soil line.

*Branch diameter.*—0.5 cm at the base of a 21-cm long branch.

*Branch length.*—21 cm.

*Internode length.*—2-5 cm.

*Anthocyanin.*—N/A.

Leaves:

*Quantity of leaves per branch.*—12 to 14. Arrangement: Opposite.

*Fragrance*.—Not fragrant.

*Shape*.—Ovate, consistent.

*Length.*—10-11 cm.

*Width.*—7-8 cm.

*Apex*.—Broadly acute.

*Base*.—Attenuate.

*Margin*.—Crenate.

*Leaf texture* (*both surfaces*).—Slightly pubescent upper surface, smooth lower surface.

*Pubescence color* (*both surfaces*).—Non-descript with naked eye.

*Venation color*.—Upper surface: Base: RHS 186A. Lower surface: RHS 186C.

*Venation pattern*.—Upper surface: Reticulate. Lower surface: Reticulate.

*Color.*—Immature leaf: Upper surface: RHS 171D in the center of the leaf, with RHS N152A margins. Lower surface: RHS 63A in the center of the leaf, irregularly transitioning to RHS 187B toward the leaf edge.

*Color*.—Mature leaf: Upper surface: RHS 39C in the center of the leaf transitioning to RHS171B, with RHS N152B margins. Lower surface: RHS 60D in the center of the leaf, irregularly transitioning to RHS 187B toward the leaf edge.

*Petiole length.*—3-7 cm.

*Petiole diameter.*—0.2-0.3 cm.

*Petiole color.*—RHS 145C.

Flowers and seeds: Flowers and seeds have not been observed to date.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Pernonspora lamii*). This pathogen has been observed in stock materials grown closely together in cooler growing seasons.

What is claimed is:

1. A new and distinct *Plectranthus scutellarioides* plant called 'UF12-6-2' as described and illustrated herein.

* * * * *